United States Patent
Koyasu et al.

(10) Patent No.: US 10,599,811 B2
(45) Date of Patent: Mar. 24, 2020

(54) MEDICAL IMAGE STORAGE PROCESSING APPARATUS, METHOD, AND MEDIUM

(71) Applicant: FUJIFILM Corporation, Tokyo (JP)

(72) Inventors: Toshiya Koyasu, Tokyo (JP); Masayuki Murakami, Tokyo (JP)

(73) Assignee: FUJIFILM CORPORATION, Tokyo (JP)

(*) Notice: Subject to any disclaimer, the term of this patent is extended or adjusted under 35 U.S.C. 154(b) by 0 days.

(21) Appl. No.: 14/860,694

(22) Filed: Sep. 21, 2015

(65) Prior Publication Data
US 2016/0093045 A1 Mar. 31, 2016

(30) Foreign Application Priority Data

Sep. 29, 2014 (JP) ................... 2014-198312

(51) Int. Cl.
G06K 9/00 (2006.01)
G06F 19/00 (2018.01)

(52) U.S. Cl.
CPC .................. G06F 19/321 (2013.01)

(58) Field of Classification Search
CPC .................................... G06T 7/0016
See application file for complete search history.

(56) References Cited

U.S. PATENT DOCUMENTS

| | | | | |
|---|---|---|---|---|
| 5,359,513 A * | 10/1994 | Kano | ............. | G06T 3/0081 128/922 |
| 5,974,201 A * | 10/1999 | Chang | ............. | G06F 16/532 382/305 |
| 6,954,767 B1 * | 10/2005 | Kanada | ............. | G06F 16/51 |
| 7,769,216 B2 * | 8/2010 | Doi | ............. | G06F 19/321 382/128 |
| 8,090,176 B2 * | 1/2012 | Kinnstaetter | ............. | G06T 7/0012 382/130 |
| 8,285,013 B2 * | 10/2012 | Moriya | ............. | G06T 7/0012 382/128 |
| 8,630,467 B2 * | 1/2014 | Masumoto | ............. | G06F 19/321 382/128 |
| 8,867,807 B1 * | 10/2014 | Fram | ............. | G06F 19/321 382/128 |

(Continued)

FOREIGN PATENT DOCUMENTS

JP 2012-157557 A 8/2012
JP 2013-084309 A 5/2013

Primary Examiner — Avinash Yentrapati
(74) Attorney, Agent, or Firm — McGinn I.P. Law Group, PLLC.

(57) ABSTRACT

Providing a medical image storage unit that stores a medical image, an image processing unit that performs image processing on a medical image to be stored in the medical image storage unit and stores the result of the image processing in association with the medical image, and a past medical image identification unit that identifies, at a storage time point of a new storage target medical image in the medical image storage unit or at a time point before the storage time point, a past medical image related to the new storage target medical image from the medical images stored in the medical image storage unit, wherein the image processing unit performs the same image processing as that for the new storage target medical image on the identified past medical image and stores the result of the image processing in association with the past medical image.

19 Claims, 5 Drawing Sheets

(56) References Cited

U.S. PATENT DOCUMENTS

| | | | |
|---|---|---|---|
| 9,058,545 B2* | 6/2015 | Canda | G06F 19/321 |
| 2005/0113961 A1* | 5/2005 | Sabol | A61B 5/055 |
| | | | 700/182 |
| 2005/0169508 A1* | 8/2005 | Oosawa | G06T 5/009 |
| | | | 382/128 |
| 2006/0120581 A1* | 6/2006 | Eck | A61B 6/481 |
| | | | 382/128 |
| 2006/0212317 A1* | 9/2006 | Hahn | G06F 19/321 |
| | | | 705/3 |
| 2006/0228012 A1* | 10/2006 | Masuzawa | G06T 11/008 |
| | | | 382/131 |
| 2007/0160271 A1* | 7/2007 | Doi | G06F 19/321 |
| | | | 382/128 |
| 2008/0242977 A1* | 10/2008 | Sirohey | A61B 5/02007 |
| | | | 600/425 |
| 2009/0080744 A1* | 3/2009 | Sagawa | G06F 19/321 |
| | | | 382/131 |
| 2010/0231605 A1* | 9/2010 | Moriya | G06F 19/321 |
| | | | 345/619 |
| 2010/0310145 A1* | 12/2010 | Hashimoto | A61B 8/0883 |
| | | | 382/131 |
| 2011/0075900 A1* | 3/2011 | Masumoto | G06F 19/321 |
| | | | 382/128 |
| 2015/0254836 A1* | 9/2015 | Sako | A61B 1/00009 |
| | | | 382/128 |
| 2015/0302583 A1* | 10/2015 | Jeon | G06T 7/0016 |
| | | | 382/128 |
| 2016/0292498 A1* | 10/2016 | Miura | A61B 1/00009 |

* cited by examiner

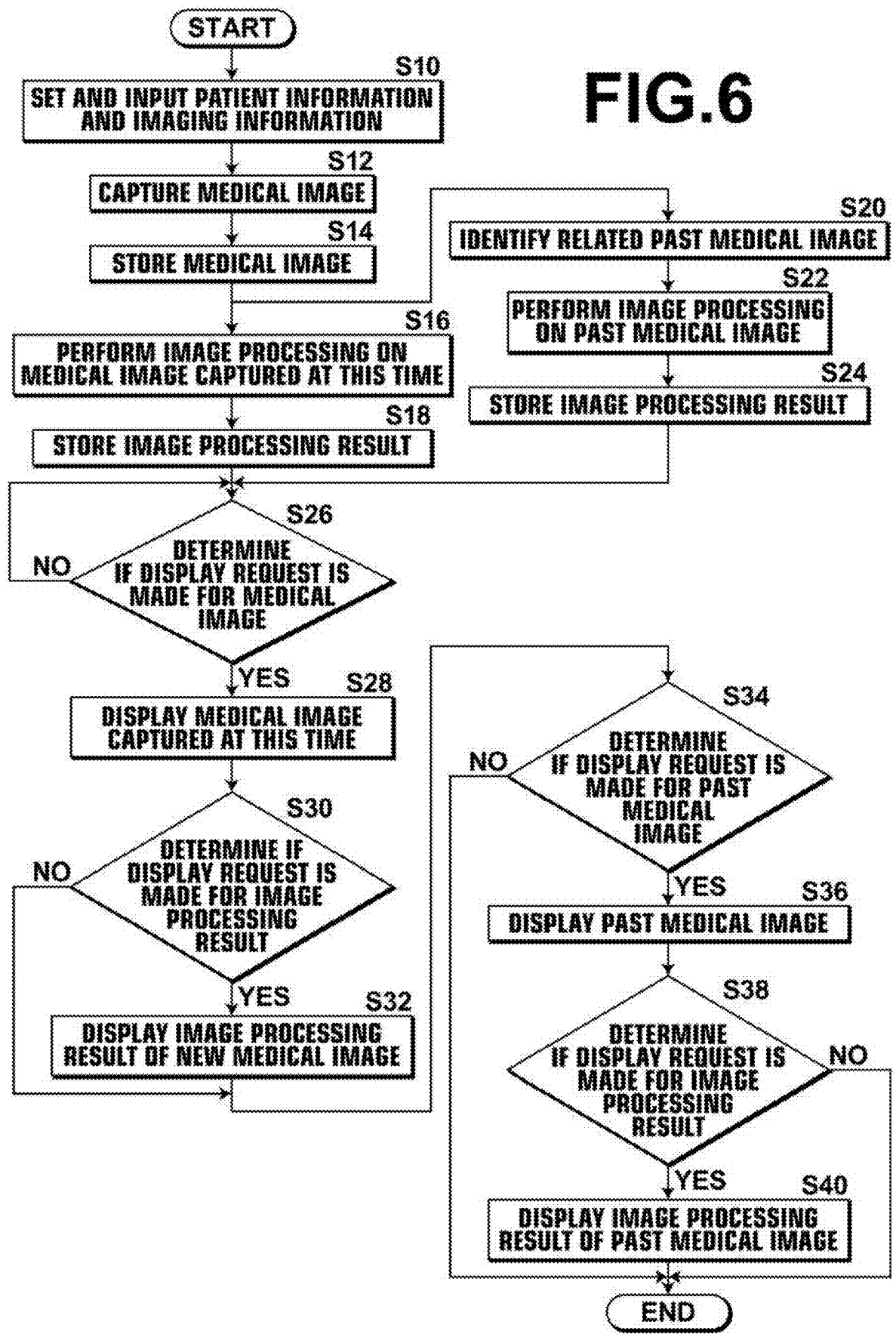

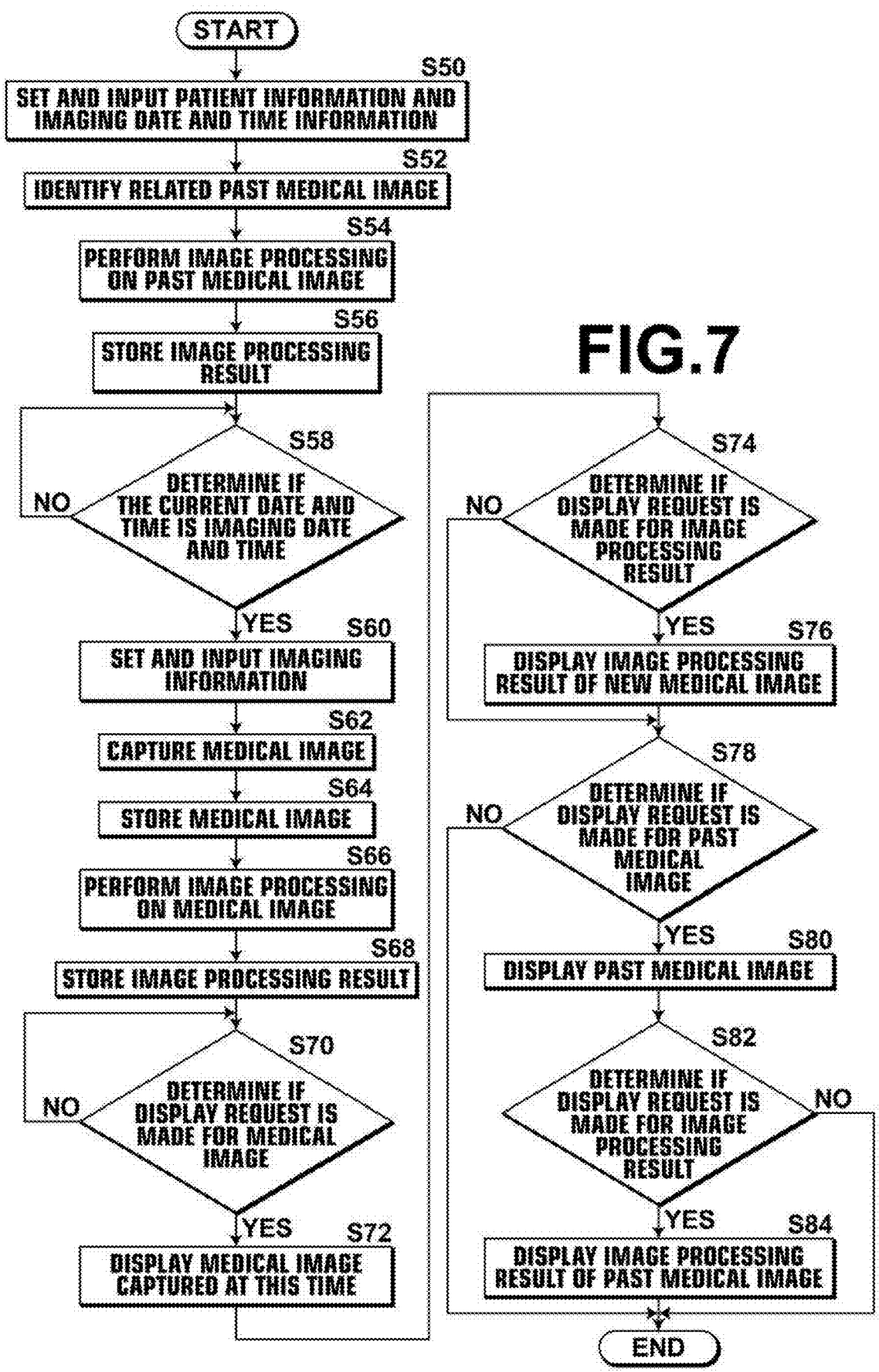

MEDICAL IMAGE STORAGE PROCESSING APPARATUS, METHOD, AND MEDIUM

CROSS-REFERENCE TO RELATED APPLICATIONS

The present application claims priority under 35 U.S.C § 119 to Japanese Patent Application No. 2014-198312 filed on Sep. 29, 2014. The above application is hereby expressly incorporated by reference, in its entirety, into the present application.

BACKGROUND

The present disclosure relates to a medical image storage processing apparatus, method, and program for storing a medical image and the result of image processing for the stored medical image in association with the image.

Recently, development of image processing for medical images has been in progress and even in two-dimensional viewers, those having very sophisticated image processing functions have been proposed. More specifically, it is practiced to perform image processing on volume data captured, for example, by a computed tomography (CT) system to extract and display anatomical features, such as pulmonary apex, liver top, and the like.

Such sophisticated image processing functions are very useful to improve diagnostic accuracy of medical images but, on the other hand, it may sometimes require several tens of seconds from the start of an image processing function by the user until the result of the processing is available, simply because of sophisticated image processing, which is undesirable from the viewpoint of diagnostic efficiency.

Hence, it is proposed that, at the timing of capturing and storing a medical image, image processing requiring a relatively long time is performed on the medical image and the result of the image processing is stored in advance.

In the meantime, when interpreting a medical image, a comparative interpretation is performed in which a medical image captured at this time and a medical image captured in the past are comparatively observed. For example, Japanese Unexamined Patent Publication No. 2012-157557 and Japanese Unexamined Patent Publication No. 2013-084309 propose to perform the same image processing on the two medical images when performing the comparative interpretation for ease of comparison between the two images.

SUMMARY

Here, when performing the comparative interpretation as described above, image processing is performed on a medical image captured at this time when it is stored and the image processing result is stored but the image processing result of a past medical image may not be sometimes stored.

For example, image processing results of past medical images may possibly be deleted due to a tight remaining storage capacity of a hard disk storing image processing results.

Further, even the image processing result of a past medical image is present, if the image processing result differs in image recognition algorithm from the image processing performed on the medical image captured at this time, the past medical image is undesirable as the comparison target.

Still further, in a case where an image processing apparatus for performing image processing itself was not incorporated in the system at the time when the past medical image was captured, no image processing result of the past medical image is stored.

Hence, it may be conceivable to perform image processing on the past medical image when performing a comparative interpretation but, in this case, while the image processing result of the medical image captured at this time is displayed instantaneously, the image processing result of the past medical image is displayed with a time delay, that is, there is a significant difference in responsiveness, thereby giving an uncomfortable feeling to the user.

Further, in a case where the display time of a medical image is restricted, such as the case where tomographic images are sequentially switched and displayed while changing the slice position, the image processing result of the past medical image may not sometimes be ready and unable to be displayed.

In view of the circumstances described above, the present discloser provides a medical image storage processing apparatus, method, and program capable of instantaneously displaying the result of each image processing when performing a comparative interpretation between a newly captured medical image and a past medical image.

A medical image storage processing apparatus of the present disclosure includes a medical image storage unit that stores a medical image, an image processing unit that performs image processing on a medical image to be stored in the medical image storage unit and stores the result of the image processing in association with the image processing target medical image, and a past medical image identification unit that identifies, at a storage time point of a new storage target medical image in the medical image storage unit or at a time point before the storage time point, a past medical image related to the new storage target medical image from the medical images stored in the medical image storage unit, wherein the image processing unit performs the same image processing as that for the new storage target medical image on the past medical image identified by the past medical image identification unit and stores the result of the image processing in association with the past medical image.

In the foregoing medical image storage processing apparatus of the present disclosure, the past medical image identification unit may identify the related past medical image at a time point when the new storage target medical image is detected to have been stored in the medical image storage unit.

Further, the past medical image identification unit may identify the related past medical image before the new storage target medical image is captured.

Still further, the past medical image identification unit may obtain imaging schedule information and may identify the related past medical image before the new storage target medical image is captured based on the obtained imaging schedule information.

Further, the past medical image identification unit may identify a medical image of the same patient as that who is the imaging target of the new storage target medical image as the related past medical image.

Still further, the past medical image identification unit may identify a medical image of the same patient as that who is the imaging target of the new storage target medical image and captured at a past time point nearest to the time point when the new storage target medical image is captured as the related past medical image.

Further, the past medical image identification unit may identify a medical image of the same patient as that who is the imaging target of the new storage target medical image and subjected to different image processing from that which is to be performed on the new storage target medical image as the related past medical image.

Still further, the past medical image identification unit may identify the related past medical image based on imaging condition information of the new storage target medical image.

Further, the past medical image identification unit may identify the related past medical image based on body part information of the new storage target medical image.

Still further, the image processing unit may perform image processing on the related past medical image at a scheduled time.

A medical image storage processing method of the present disclosure is a method for storing a medical image, performing image processing on the medical image to be stored, and storing the result of the image processing in association with the image processing target medical image, wherein at a storage time point of a new storage target medical image or at a time point before the storage time point, a past medical image related to the new storage target medical image is identified from the stored medical images, and the same image processing as that for the new storage target medical image is performed on the identified past medical image and the result of the image processing is stored in association with the past medical image.

A medical image storage processing program of the present disclosure is a program for causing a computer to perform the steps of performing image processing on a medical image to be stored and storing the result of the image processing in association with the image processing target medical image, identifying, at a storage time point of a new storage target medical image or at a time point before the storage time point, a past medical image related to the new storage target medical image from the stored medical images, and performing the same image processing as that for the new storage target medical image on the identified past medical image and storing the result of the image processing in association with the past medical image.

According to the medical image storage processing apparatus, method, and program of the present disclosure, at a storage time point of a new storage target medical image in the medical image storage unit or at a time point before the storage time point, a past medical image related to the new storage target medical image is identified, and the same image processing as that for the new storage target medical image is performed on the identified past medical image, and the result of the image processing is stored in association with the past medical image. Therefore, prior to performing a comparative interpretation between a newly captured medical image and a past medical image, a related past image may be identified and the image processing result of the past medical image may be stored in advance. Thus, when performing the comparative interpretation, the image processing result of each medical image may be displayed instantaneously.

BRIEF DESCRIPTION OF THE DRAWINGS

FIG. 6 is a flowchart for explaining an operation of the medical image management system that uses one embodiment of the medical image storage processing apparatus, method, and program of the present disclosure.

FIG. 7 is a flowchart for explaining an example of identifying a past medical image based on imaging schedule information set and registered by the user.

DETAILED DESCRIPTION OF THE PREFERRED EMBODIMENTS

Figure 1:
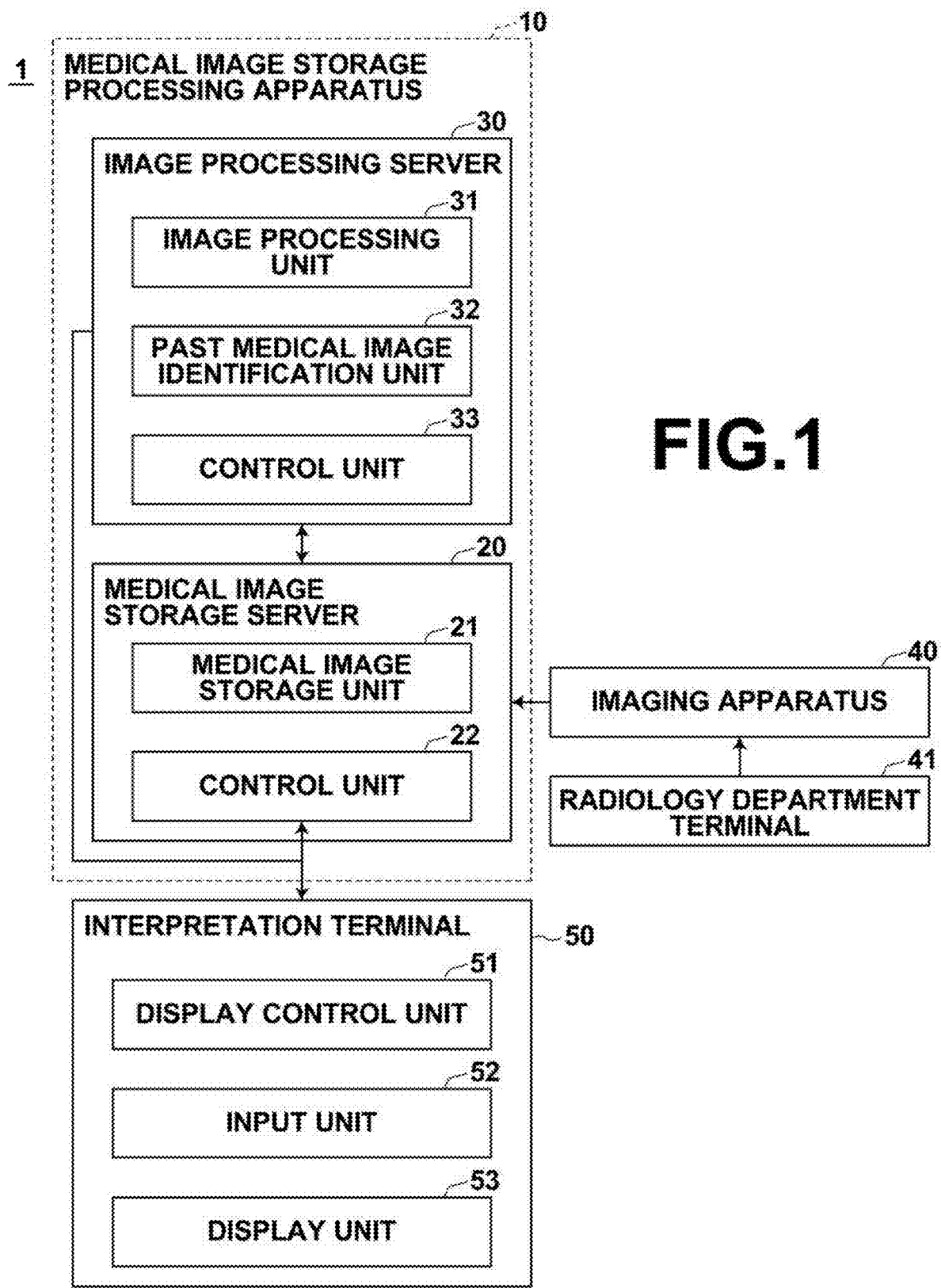
FIG. 1 is a block diagram of a medical image management system that uses one embodiment of the medical image storage processing apparatus, method, and program of the present disclosure, illustrating a schematic configuration thereof.

Hereinafter, a medical image management system that uses one embodiment of the medical image storage processing apparatus, method, and program of the present disclosure will be described in detail with reference to the accompanying drawings. FIG. 1 is a block diagram of a medical image management system 1 of the present embodiment, schematically illustrating a configuration thereof.

As illustrated in FIG. 1, the medical image management system 1 of the present embodiment includes a medical image storage processing apparatus 10, an imaging apparatus 40, a radiology department terminal 41, and an interpretation terminal 50. The medical image storage processing apparatus 10, the imaging apparatus 40, and the interpretation terminal 50 are connected to each other via a network, such as a wired or wireless LAN or an internet circuit.

The medical image storage processing apparatus 10 will be described first. The medical image storage processing apparatus 10 includes a medical image storage server 20 and an image processing server 30.

The medical image storage server 20 includes a medical image storage unit 21 that stores a medical image captured by the imaging apparatus 40 and a control unit 22.

The medical image storage unit 21 includes a storage device, such as a hard disk, for storing a medical image. The medical image is stored along with auxiliary information that complies with the DICOM standard. The auxiliary information includes, for example, patient information and imaging information. The patient information includes identification information for identifying the patient, the name of the patient, gender, birth date, and the like. The imaging information includes identification information for identifying imaging, date and time of imaging, imaging conditions, and the like. The imaging conditions include the body part, the number of images when performing a plurality of series of imaging operations, the slice thickness when imaging a tomographic image, imaging direction, modality information, and the like.

The control unit 22 controls the entire medical image storage server 20 and includes a central processing unit (CPU). The control unit 22 controls receiving of a medical image and auxiliary information thereof outputted from the imaging apparatus 40 and stores the received medical image and auxiliary information in association with each other in the medical image storage unit 21. Further, in response to a request from the interpretation terminal 50, the control unit 22 reads out an interpretation target medical image from the medical image storage unit 21 and outputs the interpretation target medical image to the interpretation terminal 50.

The image processing server 30 includes an image processing unit 31, a past medical image identification unit 32, and a control unit 33. The image processing server 30 is a computer on which one embodiment of the medical image storage processing program of the present disclosure is installed. The execution of the medical image storage processing program by a central processing unit (CPU) causes the image processing unit 31 and the past medical image identification unit to function. The foregoing medical image storage processing program may be a medical image storage processing program recorded on a recording medium, such as a CD-ROM or the like, or down loaded from a server or the like via the Internet.

The image processing unit 31 performs image processing on a medical image stored in the medical image storage server 20 and stores the result of the image processing in association with the image processing target medical image. The control unit 33 of the image processing server 30 of the present embodiment monitors whether or not a medical image captured by the imaging apparatus 40 is stored in the medical image storage unit 21 of the medical image storage server 20. Then, when the medical image is detected to have been stored in the medical image storage unit 21 by the control unit 22, the image processing unit 31 automatically performs predetermined image processing on the storage target medical image and stores the result of the image processing. At this time, an identifier for identifying the stored result of the image processing is generated and outputted to the medical image storage server 20, which is appended to the image processing target medical image and stored. The identifier associates the storage target medical image with the result of the image processing of the medical image.

The image processing performed on a medical image may include, for example, processing for extracting an anatomical feature of an organ, such as pulmonary apex, liver top, cardiac apex, or the like, from a medical image, processing for extracting a lung segment, a rib, or a spine from the medical image, and the processing for extracting a lesion area, such as an abnormal tissue pattern, a pulmonary nodule, or the like. For these processing operations, the already known processing operations may be used. Further, image processing operations other than those described above may also be performed. In addition, the number of image processing operations performed on one medical image is not limited to one operation and a plurality of image processing operations may be performed.

When the medical image is stored in the medical image storage unit 21, the past medical image identification unit 32 searches for and identifies a past image related to the new storage target medical image from a plurality of medical images already stored in the medical image storage unit 21. More specifically, the past medical image identification unit 32 of the present embodiment identifies the related past medical image at the time when the new storage target image is detected to have been stored in the medical image storage unit 21 by the control unit 33 of the image processing server 30.

The past medical image identification unit 32 of the present embodiment identifies, as the related past medical image, a medical image of the same patient as that who is the imaging target of the new storage target medical image and imaged at a past time point nearest to the time point when the new storage target medical image is captured. More specifically, in a case, for example, where a new medical image is captured for patient A on Apr. 1, 2014, and, as medical images captured in the past for the same patent A, a medical image obtained on Mar. 10, 2014, a medical image obtained on Dec. 2, 2013, and a medical image obtained on Jun. 6, 2013 are stored, the medical image obtained on Mar. 10, 2014 is identified as the related past medical image.

In the case where the medical image captured most recently is identified as the related past medical image as described above, it is preferable to search for and identify a medical image obtained by imaging the same region as that of the new storage target medical image, but a medical image obtained by imaging a different region may be identified. Further, the related past medical image is identified with reference to the auxiliary information appended to the medical image.

Further, not only the medical image captured most recently but also medical images captured at a plurality of past time points from the last, such as a past medical image captured at one time before the last or past medical images captured at two times before the last may be identified as the related past medical images. The number of related past medical images may be set arbitrarily by the user. The number may be set using, for example, the input unit 52 of the interpretation terminal 50.

Note that the past medical images related to the new storage target medical image are not limited to the foregoing medical images, and the other examples will be described in detail later.

The related past medical image identified by the past medical image identification unit 32 is read out from the medical image storage unit 21 of the medical image storage server 20 by the image processing unit 31. The image processing unit 31 performs the same image processing as that for the new storage target medical image on the read-out past medical image and stores the result of the image processing in association with the past medical image. The association between the past medical image and the result of the image processing thereof are implemented by appending an identifier for identifying the result of the image processing to the medical image as described above.

Note that, when performing the image processing on the past medical image as described above, if the same image processing as that for the new storage target medical image is already performed, the image processing may be omitted.

In a case where image processing is already performed on the past medical image, but the image processing is different image processing from that for the new storage target medical image, it is preferable that the same image processing as that for the new storage target medical image is performed on the past medical image and the result of the image processing and the identifier are updated. The term "different image processing" as used herein may include not only the image processing which is different in image processing result, but also the image processing which is different in program version or program algorithm even though it extracts the same anatomical feature from the medical image.

Further, in a case where a plurality of image processing operations is to be performed on the new storage target medical image, and image processing is already performed on the past medical image, but it is only a part of the plurality of image processing operations, a remaining image processing operation is preferably performed on the past medical image other than the part of the plurality of image processing operations and to update the result of the image processing and the identifier. In this case, not only the remaining image processing operation, but also the part of the plurality of image processing operations may be performed again.

The control unit 33 controls the entire image processing server 30. The control unit 33 of the present embodiment, in particular, monitors whether or not a new medical image is stored in the medical image storage unit 21 of the medical image storage server 20 as described above.

The imaging apparatus 40 performs imaging of a patient to obtain a medical image and outputs the medical image to the medical image storage server 20. The modalities that may be used as the imaging apparatus 40 include, for example, a computed tomography (CT) imaging system, a magnetic resonance imaging (MRI) system, an imaging system using a flat panel detector (FPD), a computed radiography (CR) imaging system, and the like.

The radiology department terminal 41 is connected to the imaging apparatus 40. The radiology department terminal 41 receives setting inputs of the foregoing patient information of an imaging target patient and the foregoing imaging information when imaging a medical image. The patient information and the imaging information set and inputted at the radiology department terminal 41 are outputted to the medical image storage server 20 along with the medical image.

The interpretation terminal 50 receives the medical image read out from the medical image storage unit 21 and the result of the image processing of the medical image stored in the image processing unit 31 and displays the medical image and the result of the image processing. More specifically, the interpretation terminal 50 includes a display control unit 51, an input unit 52, and a display unit 53.

The input unit 52 accepts various types of setting inputs by the user, and includes input devices, such as a mouse and a keyboard. The input unit 52 according to the present embodiment, in particular, accepts a setting input of identification information of a patient and setting inputs of requests for displaying a medical image of the patient and the image processing result of the medical image.

The input unit 52 also accepts, when accepting the request for displaying a medical image, a selection of a display target medical image. More specifically, the input unit 52 accept the selection of a display target medical image by, for example accepting a selection of at least one of a plurality of thumbnail images displayed on the display unit 53. The selection target medical images include, for example, a medical image newly captured at this time, a past medical image used for comparative interpretation with the newly captured medical image, and the like.

The input unit 52 also accepts a request for displaying an image processing result of a medical image. The request for displaying an image processing result may be made by displaying a menu of image processing results on the display unit 53 by, for example, clicking the right mouse button, and selecting and clicking on one of the image processing results in the menu, or by clicking on a region of interest of the medical image with the mouse once or twice.

Note that the selection of a medical image for which the image processing result is to be displayed may be made by clicking on the medical image with the mouse as describe above, or placing a mouse cursor or a cursor moved by the cursor key on the medical image.

The display control unit 51 outputs the request for displaying a medical image set and inputted at the input unit 52 to the medical image storage server 20, and displays a medical image read-out according to the display request on the display unit 53.

Further, the display control unit 51 displays an image processing result on the display unit 53 according to the request for displaying an image processing result set and inputted at the input unit 52. More specifically, the display control unit 51 outputs the request for displaying an image processing result set and inputted at the input unit 52 to the medical image storage server 20. When the request for displaying an image processing result is accepted, the control unit 22 of the medical image storage server 20 obtains the identifier appended to the medical image of the image processing result display target and outputs the identifier to the image processing server 30.

The control unit 33 of the image processing server 30 reads out the image processing result corresponding to the inputted identifier from the image processing unit 31 and outputs the image processing result to the display control unit 51 of the interpretation terminal 50. The display control unit 51 displays the image processing result inputted in the manner described above on the display unit 53.

Figure 2:
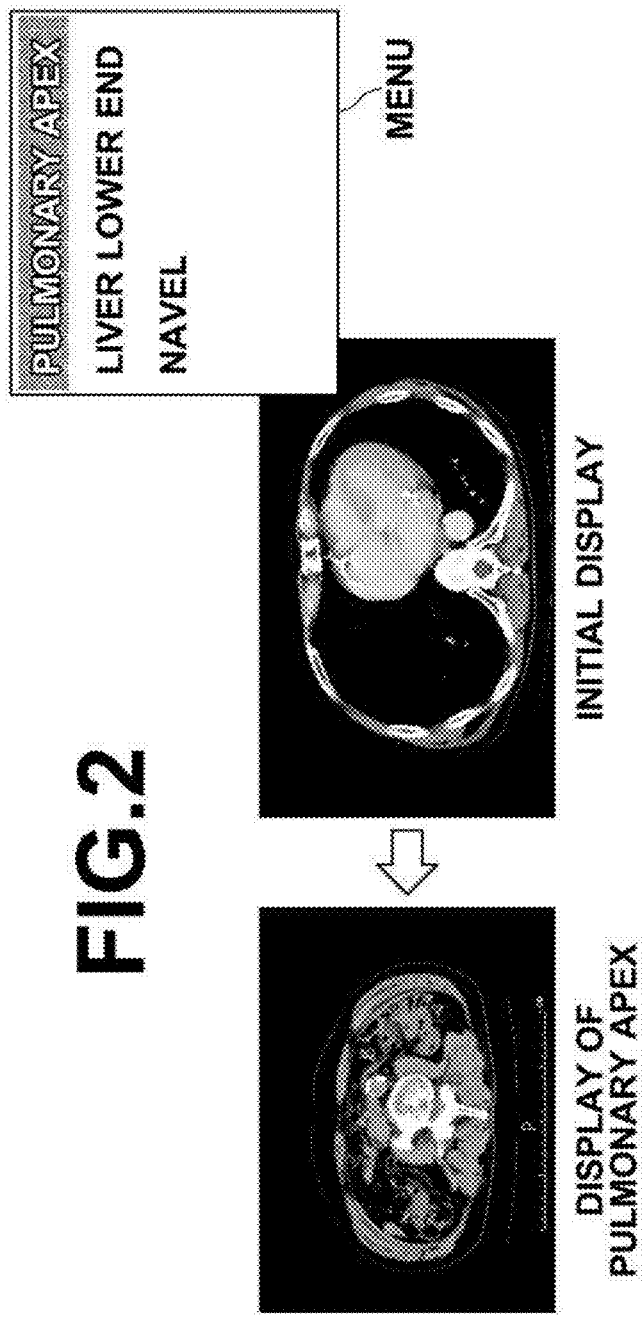
FIG. 2 shows an example of displaying an extraction processing result of an upper end portion of lung fields.

Here, a display example of an image processing result will be described. FIG. 2 shows an example of displaying an extraction processing result of the pulmonary apex. A tomographic image before a display request of an image processing result is shown on the right in FIG. 2. For example, if the right mouse button is clicked by the user under the state of the tomographic image shown on the right in FIG. 2, a selection menu of image processing results is displayed, as shown in FIG. 2. Then, if the "pulmonary apex" is selected in the selection menu, the display is switched to a tomographic image that includes the pulmonary apex extracted by image processing, as shown on the left in FIG. 2. When switching the display to a tomographic image of a desired tomographic position, it has conventionally been required to sequentially change the tomographic position by, for example, continuously rotating a mouse wheel, but the present embodiment may instantaneously display a tomographic image of a desired tomographic position simply by a clicking operation.

Figure 3:
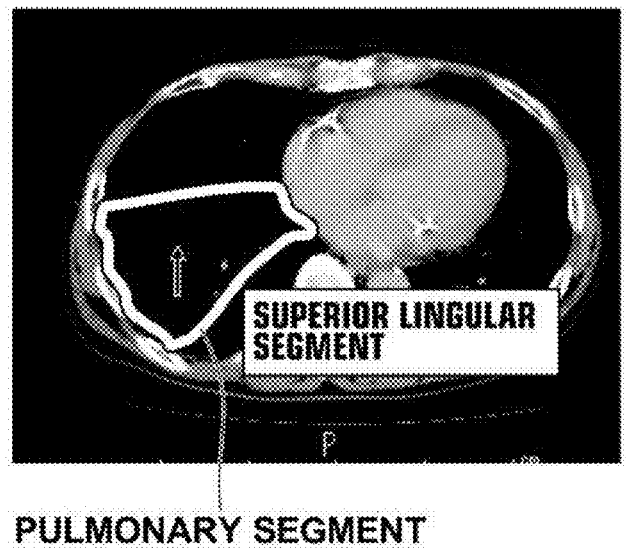
FIG. 3 shows an example of displaying an extraction processing result of a lung segment.

FIG. 3 shows an example of displaying an extraction processing result of a pulmonary segment. In the display of a tomographic image of a lung as shown in FIG. 3, if, for example, a position near an abnormal tissue pattern is clicked by the mouse, the contour of the pulmonary segment that includes the abnormal tissue pattern is labeled and displayed. In this case, the name of the pulmonary segment (e.g., "superior lingular segment") may also be displayed, as shown in FIG. 3.

Figure 4:
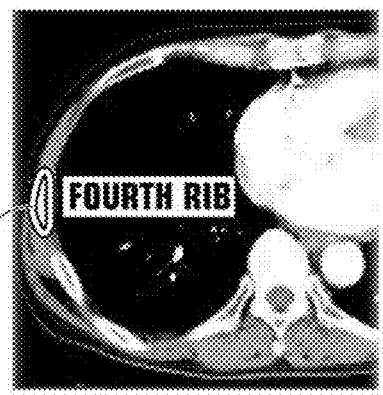
FIG. 4 shows an example of displaying an extraction processing result of a rib.

FIG. 4 shows an example of displaying an extraction processing result of a rib. In the display of a tomographic image of a lung as shown in FIG. 4, if, for example, a given rib is clicked by the mouse, the contour of the rib is labeled and displayed. In this case, the bone number of the rib may also be displayed, as shown in FIG. 4.

Figure 5:
FIG. 5 shows an example of displaying an extraction processing result of a spine.

FIG. 5 shows an example of displaying an extraction processing result of a spine. In the display of a tomographic image as shown in FIG. 5, if, for example, a given vertebra in the spine is clicked by the mouse, the contour of the vertebra is labeled and displayed. In this case, the bone number of the vertebra may also be displayed, as shown in FIG. 5.

Next, an operation of the medical image management system 1 of the present embodiment will be described with reference to the flowchart shown in FIG. 6.

First, patient information and imaging information are set and inputted at the radiology department terminal 41 (S10). Then, based on the set and inputted imaging information, a medical image is captured by the imaging apparatus 40 (S12). The medical image captured by the imaging apparatus 40, and the set and inputted patient information and imaging information are outputted to the medical image storage server 20, and auxiliary information, including the patient information and the imaging information, is appended to the medical image before being stored in the medical image storage unit 21 (S14).

When the medical image is stored in the medical image storage unit 21, the storage of a new medical image is detected by the control unit 33 of the image processing server 30, and the image processing unit 31 automatically performs predetermined image processing on the storage target medical image according to the detection (S16), and stores the result of the image processing (S18).

In the meantime, when the storage of a new medical image is detected by the control unit 33, the past medical image identification unit 32 identifies a past medical image related to the new storage target medical image at the time of the detection (S20). More specifically, the past medical image identification unit 32 of the present embodiment identifies, as the related past medical image, a medical image of the same patient as that who is the imaging target of the new storage target medical image and imaged at a past time nearest to the imaging time of the new storage target medical image, as described above.

Then, the past medical image identified by the past medical image identification unit 32 is read out from the medical image storage unit 21 of the medical image storage server 20 by the image processing unit 31, and the image processing unit 31 performs the same image processing as that for the new storage target medical image on the read-out past medical image (S22), and stores the result of the image processing in association with the past medical image (S24).

In this way, the medical image newly captured at this time and the image processing result thereof, and the related past medical image and the imaging processing result thereof are stored before a medical image interpretation is performed by the user. Thereafter, if the user wants to observe the medical image newly captured at this time, a display request of the medical image is set and inputted using the input unit 52 (S26, YES), and the display request is outputted to the medical image storage server 20 and the medical image newly captured at this time is read out from the medical image storage unit 21. The read-out medical image is outputted to the display control unit 51, and the display control unit 51 displays the inputted medical image on the display unit 53 (S28).

Then, if the user wants to observe the image processing result of the new medical image displayed on the display unit 53, a display request is set and inputted, for example, by clicking once on the medical image (S30, YES), and the display request is outputted to the medical image storage server 20. When the display request is inputted, the control unit 22 of the medical image storage server 20 obtains the identifier of the image processing target medical image and outputs the identifier to the image processing server 30. The control unit 33 of the image processing server 30 reads out the image processing result corresponding to the inputted identifier from the image processing unit 31 and outputs the image processing result to the display unit 51 of the interpretation terminal 50. Then, the display control unit 51 displays the inputted image processing result on the display unit 53 (S32).

Next, if the user wants to perform a comparative interpretation with a past medical image captured most recently with respect to the same patient, a display request for that is set and inputted using the input unit 52 (S34, YES), and the display request is outputted to the medical image storage server 20 and the most recent past medical image is read out from the medical image storage unit 21. The read-out past medical image is outputted to the display control unit 51, and the display control unit 51 displays the inputted past medical image on the display unit 53 (S36). Here, the newly captured medical image and the past medical image are preferably displayed side-by-side for the comparative interpretation.

Then, if the user wants to observe the image processing result of the past medical image displayed on the display unit 53, a display request is set and inputted, for example, by clicking once on the past medical image using the input unit 52 (S38, YES), and the display request is outputted to the medical image storage server 20. When the display request for the image processing result is inputted, the control unit 22 of the medical image storage server 20 obtains the identifier of the image processing target past medical image and outputs the identifier to the image processing server 30. The control unit 33 of the image processing server 30 reads out the image processing result corresponding to the inputted identifier from the image processing unit 31 and outputs the image processing result to the display unit 51 of the interpretation terminal 50. Then, the display control unit 51 displays the inputted image processing result of the past medical image on the display unit 53 (S40).

According to the medical image management system 1 of the foregoing embodiment, a past medical image related to a new storage target medical image is identified at a storage time point of the new storage target medical image in the medical image storage unit 21 or at a time point before the storage time point, the same image processing as that for the new storage target medical image is performed on the identified past medical image, and the result of the image processing is stored in association with the past medical image. Therefore, prior to performing a comparative interpretation between a newly captured medical image and a past medical image, a related past image may be identified and the image processing result of the past medical image may be stored in advance. Thus, when performing the comparative interpretation, the image processing result of each medical image may be displayed instantaneously.

In the description of the foregoing embodiment, the medical image captured at this time and the image processing result thereof are displayed first, then the past medical image and the image processing result thereof are displayed. But the present disclosure is not limited to this and, for example, an arrangement may be adopted in which a request instruction to perform a comparative interpretation between the medical image captured at this time and the past medical image is accepted, and the medical image captured at this time and the image processing result thereof, and the past medical image and the image processing result thereof are displayed at the same time. In this case, no uncomfortable feeling due to difference in responsiveness is given to the user, because the medical image captured at this time and the image processing result thereof, and the past medical image and the image processing result thereof may be displayed at the same time.

Further, in the medical image management system 1 of the foregoing embodiment, the past medical image identification unit 32 searches for and identifies a related past image at the time when a new storage target medical image is detected to have been stored in the medical image storage unit 21. But the timing of identifying the related past medical image is not limited to this, and the related past medical image may be identified before the time when the new storage target medical image is stored, then the same image processing as that for the new storage target image may be performed on the past medical image, and the image processing result may be stored.

Hereinafter, a specific example of the case will be described with reference to the flowchart shown in FIG. 7. Here, a description will be made of a case in which, based on imaging schedule information of a medical image set and registered by the user in advance, a related past medical image is identified at a time point before the imaging schedule time.

If the user wants to make an appointment for the imaging date and time of a medical image of a given patient, information, including the patient information and imaging date and time information, is set and inputted at the radiology department terminal 41 and registered, as imaging schedule information (S50). Then, at the time when the imaging schedule information is set and registered or at a scheduled time after the imaging schedule information is set and registered, and before the imaging date and time, the past medical image identification unit 32 searches for and identifies a related past medical image based on the set and registered patient information (S52). More specifically, a medical image of the same patient as that of the set and registered patient information and imaged at a past time nearest to the set and registered imaging time is identified as the related medical image, as in the foregoing embodiment.

Then, as in the foregoing embodiment, the past medical image identified by the past medical image identification unit 32 is read out from the medical image storage unit 21 by the image processing unit 31, and the image processing unit 31 performs the same image processing as that to be performed on a medical image to be newly captured on the read-out past medical image (S54), and the image processing result is stored in association with the past medical image (S56).

Then, when the imaging date and time in the imaging schedule information comes after the image processing result of the past medical image is stored in the manner described above, imaging information is set and inputted at the radiology department terminal 41 by the user (S60).

Then, based on the set and inputted imaging information, a new medical image is captured in the imaging apparatus 40 (S62). The medical image captured by the imaging apparatus 40, and the set and inputted patient information and imaging information are outputted to the medical image storage server 20, and the medical image is stored in the medical image storage unit 21 after auxiliary information, including the patient information and the imaging information, is appended to the medical image (S64).

When the medical image is stored in the medical image storage unit 21, the control unit 33 of the image processing server 30 detects that a new medical image is stored, and the image processing unit 31 the image processing unit 31 automatically performs predetermined image processing on the storage target medical image (S66), and stores the result of the image processing (S68).

Note that the operations from S70 to S84 are identical to those of S26 to S40 in the flowchart of FIG. 6.

So far, the description has been made of a case where a related past medical image is identified based on the imaging schedule information set and registered in advance before the reserved imaging time.

Further, in the description of the foregoing embodiment, a medical image captured most recently is identified as the past medical image related to the new storage target medical image, but not limited to this and, for example, a past medical image of the same patient as that in the new storage target medical image and whose image processing result is not stored at the present time may be identified as the related past medical image. The determination as to whether or not the image processing result of a past medical image is stored may be made by confirming whether or not an identifier is appended to the past medical image.

Otherwise, a past medical image of the same patient as that in the new storage target medical image and subjected to different image processing from that to be performed on the new storage target medical image may be identified as the related past medical image. The term "different image processing" as used herein may include not only the image processing which is different in image processing result, but also the image processing which is different in program version or program algorithm even though it extracts the same anatomical feature from the medical image. In this case, the version information or the algorithm information of the image processing program may be included in the auxiliary information of the medical image.

Further, a past medical image of the same patient as that in the new storage target medical image and captured with the same imaging conditions as those of the new storage target medical image may be identified as the related past medical image. The imaging conditions may include, for example, the slice thickness if the medical image is a tomographic image, the number of images to be captured in a case where a plurality of imaging operations is performed as a series of imaging operations, other than the body part described above.

Note that the condition when identifying a related past medical image may be a combination of the conditions described above and, for example, if a medical image is captured with a plurality of imaging conditions on the most recent date of imaging, a medical image captured on the most recent date of imaging and with the same imaging conditions may be identified as the related past medical image. Combining a plurality of conditions in this way allows a more relevant past medical image to be identified.

Further, image processing for the related past medical image may be performed at a scheduled time. For example, in a case where the image processing server 30 is connected to a plurality of imaging apparatuses 40 and image processing is performed on the medical images outputted from the plurality of imaging apparatuses 40, the burden of the hardware for performing image processing is increased during the daytime, so that performance of the processing of the past medical image during this time period may result in reduced processing efficiency. Hence, for example, in a case where imaging schedule information for a new medical image is set, as described above, image processing may be performed on the past medical image at a time point before the date and time of the imaging and during the time in which there is a margin in the processing capacity of the hardware for performing image processing. For example, image processing is preferably performed on the past medical image during early morning time or night time.

Still further, as the past medical image related to a new storage target medical image, a medical image of the same patient is identified in the description of the foregoing embodiment. But, for example, if a past medical image of a different patient is desired to be referenced as the target medical image for a comparative interpretation, the related past medical image may be identified by including a medical image of a different patient.

What is claimed is:

1. A medical image storage processing apparatus, comprising:
   a hard disk that stores a medical image; and
   a processor that is connected to the hard disk and that is configured to:

perform image processing on the medical image to be stored in the hard disk and store a result of the image processing in association with an image processing target medical image;

identify, at a storage time point of a new storage target medical image in the hard disk or at a time point before the storage time point, a past medical image related to the new storage target medical image from the medical images stored in the hard disk;

confirm whether a same image processing as that for the new storage target medical image has been administered on the identified past medical image, generate a comparison image that is comparable with the new storage target medical image by performing a same image processing on the past medical image in a case that the same image processing has not been administered on the past medical image, the comparison image in association with the past medical image, and does not perform the same image processing on the past medical image in a case that the same image processing has been administered on the past medical image, and set the past medical image as the comparison image; and display the comparison image and the new storage target medical image in a row, wherein the image processing includes extracting a predetermined feature, wherein, in a same image processing:
   a feature that is extracted by a first image processing is the same as a feature that is extracted by a second image processing; and
   a version of a program that is used for the first image processing is the same as a version of a program that is used for the second image processing, and wherein the processor identifies, as the past medical image related to the new storage target medical image, a past medical image, in a case in which at least one of a number of images when performing a plurality of series of imaging operations, or an imaging direction of the past medical image is a same as a corresponding one of the new storage target medical image.

2. The medical image storage processing apparatus of claim 1, wherein the processor is further configured to identify the past medical image related to the new storage target medical image at a time point when the new storage target medical image is detected to have been stored in the hard disk.

3. The medical image storage processing apparatus of claim 1, wherein the processor is further configured to identify the past medical image related to the new storage target medical image before the new storage target medical image is captured.

4. The medical image storage processing apparatus of claim 3, wherein the processor is further configured to:
   obtain imaging schedule information; and
   identify the past medical image related to the new storage target medical image before the new storage target medical image is captured based on the obtained imaging schedule information.

5. The medical image storage processing apparatus of claim 1, wherein the processor is further configured to identify a medical image of a same patient as that who is an imaging target of the new storage target medical image as the past medical image related to the new storage target medical image.

6. The medical image storage processing apparatus of claim 5, wherein the processor is further configured to identify a medical image of the same patient as that who is the imaging target of the new storage target medical image and captured at a past time point nearest to the time point when the new storage target medical image is captured as the past medical image related to the new storage target medical image.

7. The medical image storage processing apparatus of claim 5, wherein the processor is further configured to identify a medical image of the same patient as that who is the imaging target of the new storage target medical image and subjected to a different image processing from that which is to be performed on the new storage target medical image as the past medical image related to the new storage target medical image.

8. The medical image storage processing apparatus of claim 1, wherein the processor is further configured to identify the past medical image related to the new storage target medical image based on body part information of the new storage target medical image.

9. The medical image storage processing apparatus of claim 1, wherein the processor is further configured to perform image processing on the past medical image related to the new storage target medical image at a scheduled time.

10. A medical image storage processing method for storing a medical image, performing image processing on the medical image to be stored, and storing a result of the image processing in association with an image processing target medical image, wherein:
   at a storage time point of a new storage target medical image or at a time point before the storage time point, a past medical image related to the new storage target medical image is identified from the stored medical images;
   a comparison image that is comparable with the new storage target medical image is generated by performing a same image processing as that for the new storage target medical image on the identified past medical image in a case that the same image processing has not been administered on the past medical image, the comparison image is stored in association with the past medical image, and does not perform the same image processing on the past medical image in a case that the same image processing has been administered on the past medical image, the past medical image is set as the comparison image, and the comparison image and the new storage target medical image are displayed in a row;
   the image processing includes extracting a predetermined feature; and
   in a same image processing:
      a feature that is extracted by a first image processing is the same as a feature that is extracted by a second image processing;
      a version of a program that is used for the first image processing is the same as a version of a program that is used for the second image processing, and
   wherein, as the past medical image related to the new storage target medical image, a past medical image is identified in a case in which at least one of a number of images when performing a plurality of series of imaging operations, or an imaging direction of the past medical image is a same as a corresponding one of the new storage target medical image.

11. A non-transitory computer-readable recording medium containing a medical image storage processing program for causing a computer to perform:

performing image processing on a medical image to be stored and storing a result of the image processing in association with an image processing target medical image;

identifying, at a storage time point of a new storage target medical image or at a time point before the storage time point, a past medical image related to the new storage target medical image from the stored medical images;

generating a comparison image that is comparable with the new storage target medical image by performing a same image processing as that for the new storage target medical image on the identified past medical image in a case that the same image processing has not been administered on the past medical image, storing the comparison image in association with the past medical image, and does not perform the same image processing on the past medical image in a case that the same image processing has been administered on the past medical image, and setting the past medical image as the comparison image; and displaying the comparison image and the new storage target medical image in a row, wherein the image processing includes extracting a predetermined feature, wherein, in a same image processing:
  a feature that is extracted by a first image processing is the same as a feature that is extracted by a second image processing; and
  a version of a program that is used for the first image processing is the same as a version of a program that is used for the second image processing, and wherein, as the past medical image related to the new storage target medical image, a past medical image is identified in a case in which at least one of a number of images when performing a plurality of series of imaging operations, or an imaging direction of the past medical image is a same as a corresponding one of the new storage target medical image.

12. A medical image storage processing apparatus, comprising:

a hard disk that stores a medical image; and
a processor;
the processor being configured to execute:
  performing image processing on a medical image to be stored in the hard disk, and storing a result of the image processing in association with an image processing target medical image;
  identifying, at a storage time point of a new storage target medical image in the hard disk or at a time point before the storage time point, a past medical image related to the new storage target medical image from the medical images stored in the hard disk;
  confirming whether a same image processing as that for the new storage target medical image has been administered on the past medical image identified, generating a comparison image that is comparable with the new storage target medical image by performing the same image processing on the past medical image in a case that the same image processing has not been administered on the past medical image, storing the comparison image in association with the past medical image, and not performing the same image processing on the past medical image in a case that the same image processing has been administered on the past medical image, and setting the past medical image as the comparison image; and
  displaying the comparison image and the new storage target medical image in a row, wherein the image processing includes extracting a predetermined feature, wherein, in the same image processing:
  a feature that is extracted by a first image processing is the same as a feature that is extracted by a second image processing; and
  a version of a program that is used for the first image processing is the same as a version of a program that is used for the second image processing, and wherein, as the past medical image related to the new storage target medical image, a past medical image is identified in a case in which at least one of a number of images when performing a plurality of series of imaging operations, or an imaging direction of the past medical image is a same as a corresponding one of the new storage target medical image.

13. The medical image storage processing apparatus of claim 1, wherein imaging condition information of the new storage target medical image comprises identifying imaging, a date and a time of imaging, and the imaging condition, and
  wherein the imaging condition comprises a body part, the number of images when performing the plurality of series of imaging operations, a slice thickness when imaging a tomographic image, the imaging direction, and the modality information.

14. The medical image storage processing method for storing a medical image according to claim 10, wherein imaging condition information of the new storage target medical image comprises identifying imaging, a date and a time of imaging, and the imaging condition, and
  wherein the imaging condition comprises a body part, the number of images when performing the plurality of series of imaging operations, a slice thickness when imaging a tomographic image, the imaging direction, and the modality information.

15. The medical image storage processing apparatus according to claim 12, wherein imaging condition information of the new storage target medical image comprises identifying imaging, a date and a time of imaging, and the imaging condition, and
  wherein the imaging condition comprises a body part, the number of images when performing the plurality of series of imaging operations, a slice thickness when imaging a tomographic image, the imaging direction, and the modality information.

16. The medical image storage processing apparatus of claim 1, wherein the feature that is extracted by the first image processing includes an anatomical feature.

17. The medical image storage processing apparatus of claim 1, wherein, in a case where a plurality of image processing operations is to be performed on the new storage target medical image, and a part of the plurality of image processing operations is already performed on the past medical image, a remaining image processing operation is performed on the past medical image other than a part of the plurality of image processing operations.

18. The medical image storage processing apparatus of claim 1, wherein the processor identifies the imaging direction is the same as the corresponding one of the new storage target medical image.

19. The medical image storage processing apparatus of claim 1, wherein the processor identifies the modality information of the past medical image is the same as the corresponding one of the new storage target medical image.

* * * * *